(12) United States Patent
Koestlmeier et al.

(10) Patent No.: US 11,504,078 B2
(45) Date of Patent: Nov. 22, 2022

(54) METHOD FOR PRODUCING A RADIATION PROTECTION ELEMENT, RADIATION PROTECTION ELEMENT AND RADIATION PROTECTION APPARATUS

(71) Applicant: Mavig GmbH, Munich (DE)

(72) Inventors: Manfred Koestlmeier, Putzbrunn (DE); Frank Klein, Erding (DE); Felix Stangl, Munich (DE)

(73) Assignee: Mavig GmbH, Munich (DE)

( * ) Notice: Subject to any disclaimer, the term of this patent is extended or adjusted under 35 U.S.C. 154(b) by 237 days.

(21) Appl. No.: 16/892,816

(22) Filed: Jun. 4, 2020

(65) Prior Publication Data

US 2020/0383649 A1 Dec. 10, 2020

(30) Foreign Application Priority Data

Jun. 4, 2019 (DE) .......................... 102019003954.8

(51) Int. Cl.
*A61B 6/10* (2006.01)
*G21F 1/12* (2006.01)
*G21F 1/02* (2006.01)

(52) U.S. Cl.
CPC ............... *A61B 6/107* (2013.01); *G21F 1/02* (2013.01); *G21F 1/12* (2013.01)

(58) Field of Classification Search
CPC .............. A61B 6/107; G21F 1/02; G21F 1/12
See application file for complete search history.

(56) References Cited

U.S. PATENT DOCUMENTS

2006/0108548 A1\* 5/2006 Cadwalader .............. G21F 3/02
250/515.1

FOREIGN PATENT DOCUMENTS

| CN | 1852944 A | 10/2006 |
| DE | 102009025380 A1 | 12/2010 |
| DE | 102015208829 A1 | 11/2016 |
| WO | 98/53461 A1 | 11/1998 |
| WO | 2016/174111 A1 | 11/2016 |

\* cited by examiner

*Primary Examiner* — Nicole M Ippolito
*Assistant Examiner* — Hanway Chang
(74) *Attorney, Agent, or Firm* — Scully Scott Murphy and Presser (57) ABSTRACT

A radiation protection material (10) is arranged between at least two layers (21, 22) of at least one plastic-containing element in order to produce a radiation protection element. At least part of the gas present between the at least two layers (21, 22) is removed. The at least two layers (21, 22) are connected with each other.

19 Claims, 4 Drawing Sheets

METHOD FOR PRODUCING A RADIATION PROTECTION ELEMENT, RADIATION PROTECTION ELEMENT AND RADIATION PROTECTION APPARATUS

FIELD OF THE INVENTION

The invention relates to radiation protection elements and methods for producing the same. The invention particularly relates to radiation protection elements comprising a sheath made of a plastic-containing material and a radiation protection material arranged within the sheath.

BACKGROUND

In diagnostics and therapy as well as in operating rooms, radiation protection apparatuses for use, e.g., in interventional radiology serve to protect involved staff against occurring radiation, particularly X-ray radiation. Such radiation protection apparatuses may comprise, e.g., lower body protection shields with panels mountable to a patient table or other radiation protection elements mountable to a patient table. Different configurations of radiation protection apparatuses are also known, e.g., in the form of a mobile radiation protection cart which may comprise a lower part with flexible panels and an upper part with angled panels.

DE 10 2009 025 380 A1 discloses a radiation protection assembly comprising at least one panel made of a radiation protection material and a corresponding mounting device.

DE 10 2015 208 829 A1 discloses a radiation protection assembly for mounting on a carrier rail, said radiation protection assembly being mounted to a side of a treatment table.

For reasons of hygiene, in order to protect the radiation protection material and for other reasons, it may be desirable for radiation protection elements to comprise a sheath and a radiation protection material arranged within the internal volume of the sheath. The sheath may be a plastic sheath.

Often, there is a problem of an outer surface of the sheath exhibiting an undesirable wrinkling. Such wrinkles may impede installation of the radiation protection element. Oxidation processes of the radiation protection element may be promoted by air pockets within the wrinkles. Such wrinkles may also make it more difficult to identify whether the radiation protection material is correctly positioned within the sheath.

SUMMARY OF THE INVENTION

It is an object of the invention to provide improved radiation protection elements with a sheath and at least one radiation protection material arranged within the sheath as well as improved methods for producing such radiation protection elements. Particularly, it is an object of the invention to provide such radiation protection elements and production methods which reduce the risk of installation of the radiation protection element to a patient table or another structure being impeded, oxidation processes being promoted within the sheath, and/or it being made more difficult to identify whether the radiation protection material is correctly positioned within the sheath due to wrinkling within the sheath.

According to the invention, a method, radiation protection elements, and a radiation protection apparatus with the features recited in the independent claims are provided. The dependent claims define embodiments.

A method for producing a radiation protection element according to the invention comprises the step of arranging at least one radiation protection material between at least two layers of at least one plastic-containing element. At least part of a gas that is present between the at least two layers may be removed. For instance, this may be done by pressing on one or both layers, or by producing a partial vacuum. Alternatively or additionally, the at least two layers with the at least one radiation protection material arranged therebetween may be introduced into an inert gas atmosphere. The at least two layers are then connected with each other.

The at least one radiation protection material may comprise a layer or a plurality of layers of a radiation protection material, e.g., a layer or a plurality of layers of a two-dimensional radiation protection material.

In this method, a gas pressure in a region between the at least two layers may be reduced from an initial pressure to a processing gas pressure while the at least two layers are being connected with each other.

The processing gas pressure may be selected such that a gas pressure is less than 1 bar at a temperature of 23° C. inside a sheath of the radiation protection material formed by connecting the at least two layers.

In this method, the at least two layers may be connected with each other in an inert gas atmosphere. In comparison to air, the inert gas atmosphere may have a reduced oxygen content.

At a temperature of 23° C., the gas pressure inside the sheath may preferably be less than 0.995 bars, further preferably less than 0.99 bars, further preferably less than 0.98 bars, further preferably less than 0.97 bars, further preferably less than 0.96 bars, further preferably less than 0.95 bars, further preferably less than 0.93 bars, further preferably less than 0.9 bars.

In order to remove at least part of the gas present between the at least two layers, at least one of the layers may be pressed toward the radiation protection material. One or both layers may be pressed against the radiation protection material or against a shaped part or carrier material that may optionally also be present between the layers.

At least one of the layers may be pressed toward the radiation protection material by means of a movable element of a welding apparatus that connects the at least two layers with each other.

In order to remove at least part of the gas present between the at least two layers, the at least two layers and the radiation protection material may alternatively or additionally be placed in a processing chamber with a gas pressure reduced relative to ambient pressure.

The radiation protection element, which may, e.g., have the shape of a panel, may be produced by vacuum drawing.

In the method, when the at least two layers are being connected, the gas pressure inside the processing chamber may preferably be less than 1 bar, preferably less than 0.995 bars, further preferably less than 0.99 bars, further preferably less than 0.98 bars, further preferably less than 0.97 bars, further preferably less than 0.96 bars, further preferably less than 0.95 bars, further preferably less than 0.93 bars, further preferably less than 0.9 bars while performing the step of connecting the two layers. Inside the processing chamber, an inert gas atmosphere may be present. In comparison to air, the inert gas atmosphere may have a reduced oxygen content.

The at least two layers may be connected with each other along a connecting line which completely or partially extends around the radiation protection material.

In the method, the at least two layers may be connected with each other along at least three sides of the radiation protection material, e.g., by means of high-frequency welding.

In the method, the at least two layers may be connected with each other along all four sides of the radiation protection material, e.g., by means of high-frequency welding.

The connection along the respective sides may be achieved in one single step.

The connecting line completely or partially extending around the radiation protection material may be substantially airtight.

The at least two layers may be connected with each other along an additional connecting line which does not extend around the radiation protection material.

The additional connecting line may be substantially airtight.

The method may comprise a step of mounting a fixing member, e.g., an eyelet ring or a mounting bar, on the inside of the additional connecting line.

The additional connecting line may be arranged within a region of the sheath that is surrounded by the connecting line.

In the method, a carrier material and/or a shaped part may be arranged between the at least two layers in addition to the radiation protection material.

The at least two layers may be separate first and second plastic-containing elements.

The at least two layers may be different regions of an individual plastic-containing element that can be folded around the radiation protection material such that the at least two layers cover the main surfaces of the radiation protection material.

The at least one plastic-containing element may comprise a plastic film, particularly a polyurethane film.

The at least one plastic-containing element may comprise a textile. The at least one plastic-containing element may comprise a plastic-coated woven or knitted fabric. The at least one plastic-containing element may comprise a woven or knitted fabric made of fibers that are coated with a plastic material.

The at least one plastic-containing element or at least one of the layers may be translucent.

The method may comprise a step of mounting a fixing member to the at least two layers for mounting the radiation protection element to a patient table or to a radiation protection cart.

The fixing member may comprise an eyelet ring or a mounting rod.

In the method, the gas pressure inside the sheath formed by the first and second layers may be reduced such that the atmospheric pressure presses the sheath planarly, particularly in a snug-fit manner, against the radiation protection material and/or against a shaped part or carrier material optionally present inside the sheath during use of the radiation protection element.

A radiation protection element according to an embodiment comprises at least one radiation protection material and a sheath with an internal volume in which the at least one radiation protection material is arranged. The internal volume has a negative gas pressure and/or contains an inert gas.

In the internal volume, a gas pressure may be less than 1 bar (measured at 23° C.).

The gas pressure in the internal volume may preferably be less than 0.995 bars, further preferably less than 0.99 bars, further preferably less than 0.98 bars, further preferably less than 0.97 bars, further preferably less than 0.96 bars, further preferably less than 0.95 bars, further preferably less than 0.93 bars, further preferably less than 0.9 bars, measured at temperatures of 23° C.

A radiation protection element according to an embodiment comprises at least one radiation protection material and a sheath with an internal volume in which the at least one radiation protection material is arranged. The sheath planarly abuts the at least one radiation protection material.

The sheath may abut the two main surfaces of the radiation protection material in a planar and snug-fit manner.

The sheath may comprise a connecting line of two layers of the sheath which completely or partially extends around the radiation protection material.

The connecting line may be a weld seam.

The connecting line may continuously extend along at least three sides of the radiation protection material.

The connecting line may continuously extend along all four sides of the radiation protection material.

The connecting line completely or partially extending around the radiation protection material may be substantially airtight.

The sheath may comprise an additional connecting line not extending around the radiation protection material.

The additional connecting line may be substantially airtight.

The sheath may comprise a fixing member, e.g., an eyelet ring or a mounting rod, inside the additional connecting line.

The additional connecting line may be arranged within a region of the sheath, said region being surrounded by the connecting line.

In addition to the radiation protection material, the radiation protection element may comprise a carrier material and/or a shaped part in the internal volume of the sheath.

The sheath may comprise a plastic film, particularly a polyurethane film.

The sheath may comprise a textile or be made of a textile. For instance, the sheath may comprise or be made of a plastic-coated woven or knitted fabric. The sheath may comprise or be made of a woven or knitted fabric made of fibers that are coated with a plastic material.

The sheath may be translucent.

The radiation protection element may comprise a fixing member that is mounted to the sheath. The fixing member may be configured to mount the radiation protection element to a patient table or to a radiation protection cart. The fixing member may comprise an eyelet ring or a mounting rod.

The radiation protection element may be a panel.

The panel may be flexible.

The panel may be rigid.

The panel may be movable.

The panel may have an angled or bent shape.

A radiation protection apparatus according to an embodiment comprises a radiation protection element or a plurality of radiation protection elements according to an embodiment of the invention.

The radiation protection apparatus may comprise a lower body protection shield.

The radiation protection apparatus may comprise a patient table with a fixing apparatus to which the radiation protection element is mounted or to which the plurality of radiation protection elements is mounted.

The fixing apparatus of the patient table may be a mounting rail.

The radiation protection apparatus may comprise a radiation protection cart to which the radiation protection element or the plurality of radiation protection elements is mounted.

The radiation protection cart may comprise at least one radiation protection element according to an embodiment as an upper part and/or as a lower part. The radiation protection cart may comprise at least one flexible panel as a lower part and at least one rigid or movable angled panel as an upper part.

With respect to the radiation protection elements, production methods and radiation protection apparatuses, the radiation protection material may comprise or be lead rubber, without being limited thereto. The radiation protection material may be a material with highly absorbent properties for ionizing radiation, which may be achieved by a high percentage of highly absorbent elements (e.g., lead, tungsten, bismuth, antimony), which are integrated into a matrix structure.

Various effects and advantages may be achieved with the production method according to the invention, the radiation protection element according to the invention and the radiation protection apparatus according to the invention. By means of producing a radiation protection element with a sheath being pressed against the radiation protection material or shaped parts or carrier materials inside the sheath in a planar and snug-fit manner, the risk of wrinkling of the sheath is reduced. In turn, this reduces the risk of undesired wrinkles impeding correct installation of the radiation protection element. Oxidation processes may be reduced by decreasing the amount of gas in the internal volume of the sheath and/or by means of inert gas present in the sheath.

By means of pressing the sheath against the radiation protection material, large defects in the radiation protection material may be detected more easily, which, e.g., may occur due to aging processes of the material or incorrect use.

Visual testing whether the radiation protection material is still correctly positioned inside the sheath may be facilitated when the sheath abuts the radiation protection material in a planar and snug-fit manner.

By means of pressing the sheath against the radiation protection material, it may be determined where exactly the radiation protection material that is arranged within the sheath is located, and thus where exactly radiation protection is guaranteed. Regions with radiation protection are visible.

The planar and snug-fit abutment may particularly be achieved by means of a negative pressure in the internal volume of the sheath, which causes the ambient pressure to press the sheath against the radiation protection element or any shaped parts or carrier materials present in the internal volume when the radiation protection element is being used.

When a shaped part or carrier material is arranged inside the sheath, a safe, relative arrangement of the radiation protection material relative to the shaped part or carrier material may be guaranteed with the help of the pressure the sheath exerts toward the inside. Depending on the application, this can allow the radiation protection material to be fixed relative to the shaped part or carrier material without using an adhesive.

BRIEF DESCRIPTION OF THE DRAWINGS

In the following, the present invention is explained in detail using embodiments with reference to the figures.

DESCRIPTION OF PREFERRED EXEMPLARY EMBODIMENTS

In the following, advantageous or preferred embodiments are described in detail with reference to the figures. The features of the various embodiments may be combined with each other unless explicitly excluded in the following description. Corresponding or identical reference signs designate corresponding or identical elements.

The production method and the radiation protection elements produced therewith may be deployed in radiation protection apparatuses for use in, e.g., interventional radiology. With such radiation protection apparatuses, involved staff in diagnostics and therapy as well as in operating rooms is protected against occurring radiation, particularly X-ray radiation.

The production methods and the radiation protection elements produced therewith may particularly be applied to panels which are used as upper and lower parts of radiation protection apparatuses.

Lower parts of such radiation protection apparatuses may consist of hanging structures which are formed of individual broad panels or a plurality of narrow panels arranged to each other in an overlapping manner. In this way, radiation protection is guaranteed starting at table level toward the floor.

Upper parts may be configured as, e.g., angled or bent panels which assist in providing radiation protection above table level. The upper part may also be formed by an individual, broad and continuous panel, or the upper part may consist of a plurality of narrow panels overlapping each other.

According to embodiments of the invention, a radiation protection material, e.g., a lead rubber precut, may be placed between two layers of a plastic-containing material, e.g., plastic precuts. The radiation protection material may comprise absorbent chemical elements such as lead, tungsten, bismuth and/or antimony in a matrix.

The at least two layers may be connected to form a sheath. The two layers may be connected with each other such that the sheath produced by connecting the two layers of the plastic-containing material abuts the radiation protection material and/or materials optionally additionally present inside the sheath in a planar and snug-fit manner. Alternatively or additionally, an inert gas may be present inside the sheath so that an oxygen content inside the sheath is reduced in comparison to ambient air.

For this purpose, during production of the radiation protection element and prior to connecting the two layers with each other, the sheath may be formed, e.g., such that a region between the at least two layers is partially evacuated from gas and/or the at least two layers are connected with each other in an inert gas atmosphere. This may be achieved in a special processing atmosphere, e.g., a processing chamber with a partial vacuum in its interior, or in an inert gas atmosphere. Alternatively or additionally, at least one of the layers may be pressed planarly against the radiation protection material or a shaped part by a movable machine part while the two layers are being connected with each other.

Figure 1:
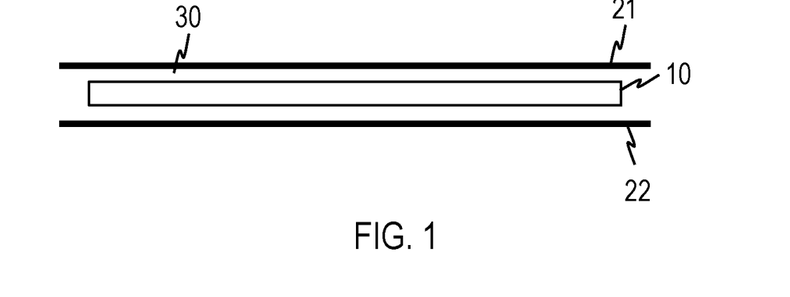
FIG. 1 is a schematic sectional view for explaining a production method according to an embodiment.
Figure 2:
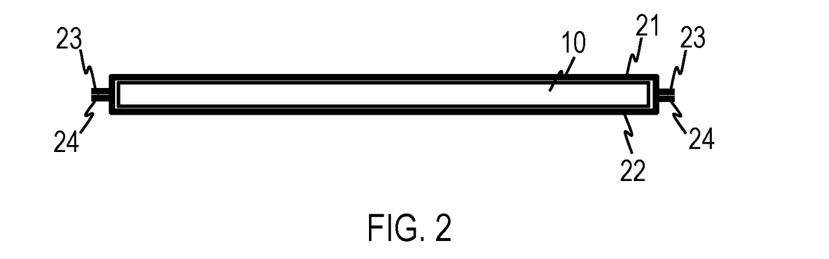
FIG. 2 is a schematic sectional view for explaining the production method according to an embodiment.

FIG. 1 and FIG. 2 show schematic sectional views for explaining the production method.

At least one radiation protection material 10 may be arranged between two layers 21, 22 of a plastic-containing material. The two layers 21, 22 may be separate two-dimensional elements, e.g., plastic precuts.

The radiation protection material 10 may be selected to absorb X-ray radiation. For instance, the radiation protection material 10 may consist of lead rubber or comprise lead rubber. The radiation protection material 10 may comprise a matrix structure with highly absorbent elements contained therein. The highly absorbent elements may comprise, e.g., lead, tungsten, bismuth and/or antimony. The radiation protection material 10 may comprise a layer or a plurality of layers of a two-dimensional radiation protection material.

The two layers 21, 22 of the sheath may be substantially airtight.

Each of the two layers 21, 22 of the sheath may consist of a plastic film, e.g., a polyurethane film. The plastic film may have a density of more than 1 g/cm$^3$, preferably of more than 1.1 g/cm$^3$. The plastic film may have a density of less than 1.5 g/cm$^3$, preferably of less than 1.3 g/cm$^3$. The plastic film may have a thickness of less than 3000 μm, preferably of at most 1000 Linn. The plastic film may have a thickness of more than 25 μm, preferably of more than 100 μm.

The two layers 21, 22 may alternatively consist of a woven or knitted fabric which is coated with a plastic material. The woven or knitted fabric may consist of plastic-coated fibers. The layers 21, 22 may comprise a plastic film which is produced with fibers.

Alternatively or additionally, one or both of the layers 21, 22 may be translucent. In this way, the correct positioning of the radiation protection material inside the radiation protection element can be checked more easily. For instance, large defects in the radiation protection material 10, which, e.g., may be caused by aging processes or incorrect use, may be detected more easily.

During production of the radiation protection element, the two layers 21, 22 may be pressed tightly against the major surfaces of the radiation protection material 10, wherein an amount of gas present in the region 30 between the two layers 21, 22 is being reduced. By means of pressing the layers 21, 22 and/or by means of creating a partial vacuum in the region 30 between the layers 21, 22, the risk of undesired wrinkling in the sheath 20 of the radiation protection element 40 may be reduced. In this state of processing, in which the amount of gas in the region 30 has been reduced, the two layers 21, 22 may be connected with each other.

In order to connect the two layers 21, 22, the two layers 21, 22 may be connected with each other along overlapping edge regions 23, 24, e.g., by means of high-frequency welding. A connecting line 25 formed in this way, which can best be seen in the top view of FIG. 3 and the sectional view of the produced radiation protection element 40 of FIG. 4, may completely extend around the radiation protection material 10. One single connecting line 25 which extends along all four sides of the radiation protection material 10, e.g., a weld seam, may be formed.

Figure 3:
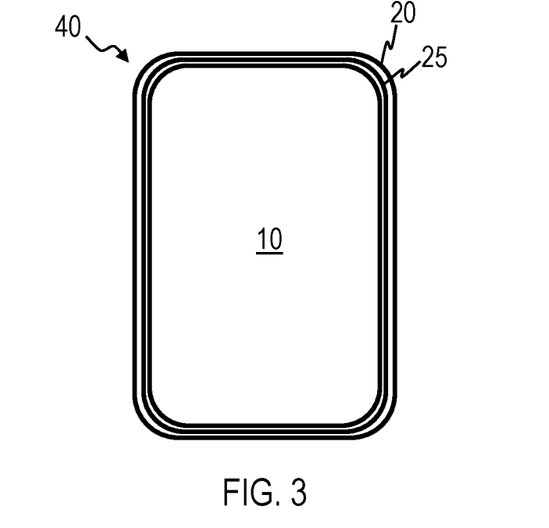
FIG. 3 is a schematic top view of a radiation protection element according to an exemplary embodiment.
Figure 4:
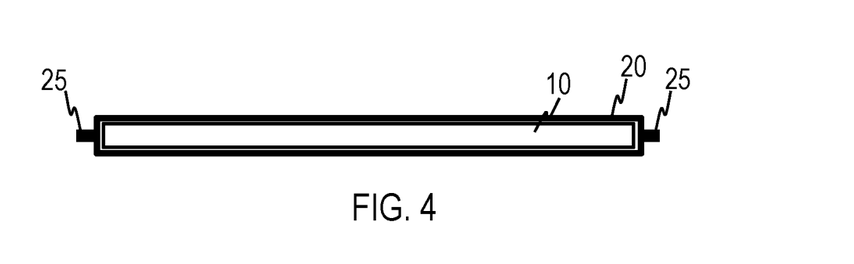
FIG. 4 is a schematic sectional view of the radiation protection element of FIG. 3.

The connecting line 25 may be substantially airtight.

Figure 5:
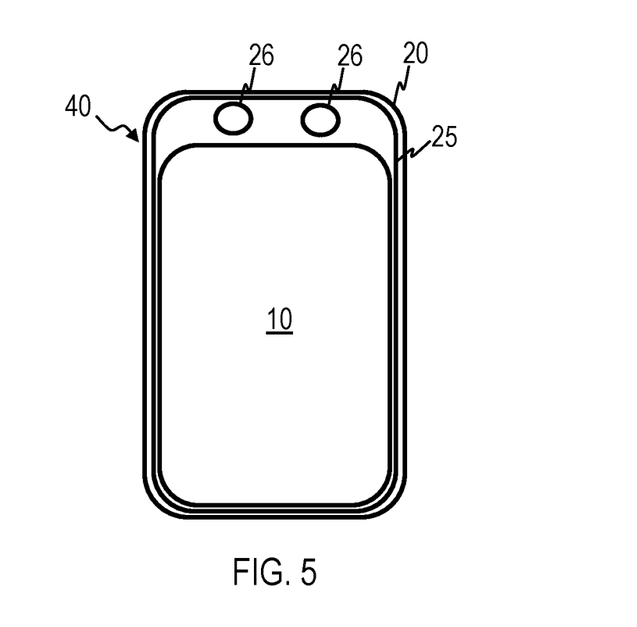
FIG. 5 is a schematic top view of a radiation protection element according to a further exemplary embodiment.

As illustrated in FIG. 5, the layers 21, 22 may additionally be connected with each other along one or a plurality of additional connecting lines 26. For instance, connecting lines 26 may be formed within the region surrounded by the outer connecting line 25 in order to attach fixing members such as eyelet rings or mounting rods within the additional connecting lines 26. If the additional connecting lines 26 are formed within the region surrounded by the outer connecting line 25, the additional connecting lines 26 are preferably configured in a substantially airtight manner. Thus, it can be ensured that the sheath 20 remains substantially free of wrinkles in the formed radiation protection element 40 and/or that inert gas remains inside the sheath also during prolonged use.

While embodiments in which the two layers 21, 22 are formed by separate elements which are connected with each other along a closed connecting line 25 have been described with reference to FIGS. 1-5, other configurations are also possible.

Figure 6:
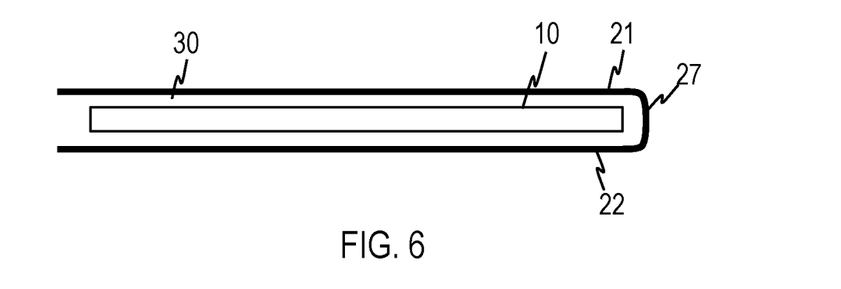
FIG. 6 is a schematic sectional view for explaining the production method according to an embodiment.

FIG. 6 is a schematic sectional view for explaining a further embodiment. The two layers 21, 22 are formed by different regions of one single planar element which, e.g., may be folded along a fold 27 such that the two layers 21, 22 are arranged on opposing major surfaces of the radiation protection material 10.

Figure 7:
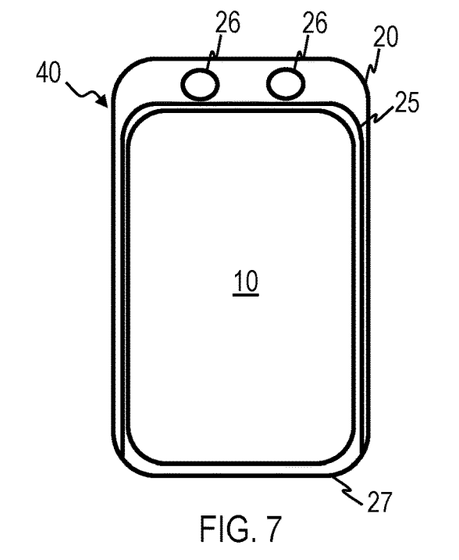
FIG. 7 is a schematic sectional view of the radiation protection element which can be produced with the method explained with reference to FIG. 6.

In such a configuration, it is not obligatory to connect the two layers 21, 22 with each other along a closed line. As schematically illustrated in FIG. 7, the two layers 21, 22 may be connected with each other, e.g., along a connecting line 25 extending around the radiation protection material 10 on only three sides, particularly in a substantially airtight manner. The connecting line 25 extends up to the fold 27 at which the plastic-containing material is folded.

As also schematically illustrated in FIG. 7, possible additional connecting lines 26, which serve to attach fixing members such as eyelet rings or mounting rods, do not necessarily have to be arranged within the region defined by the connecting line 25. For instance, the additional connecting lines 26 may also be positioned outside the regions defined by the connecting line 25. The additional connecting lines 26 do not necessarily have to be airtight.

In any of the embodiments, additional elements may be arranged inside the sheath 20, which is formed by the at least two layers 21, 22, in addition to the radiation protection material 10. Such additional elements may serve to define a three-dimensional shape or otherwise for mechanical stabilization.

Figure 8:
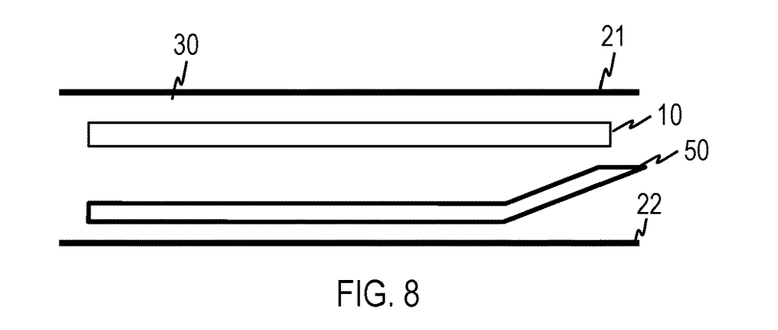
FIG. 8 is a schematic sectional view for explaining the production method according to an embodiment.

FIG. 8 exemplarily shows a configuration in which a shaped part 50 is arranged in the region 30 between the two layers 21, 22. During production of the radiation protection element 40, the sheath 20 presses the radiation protection material 10 against the shaped part 50.

Due to the creation of a negative pressure inside the sheath 20 formed by the two layers 21, 22, it is possible to secure the radiation protection material 10 at the shaped part 50 without the radiation protection material 10 compulsorily having to be attached to the shaped part 50 by means of an adhesive. In further embodiments, adhesives may optionally be used to attach the radiation protection material 10 to the shaped part 50.

The shaped part 50 may consist of plastic. Alternatively or additionally, other carrier materials may be arranged inside the sheath 20 of the radiation protection element 40 in addition to the radiation protection material 10.

A radiation protection element 40 with reduced gas pressure on the inside may be produced in different ways.

Figure 9:
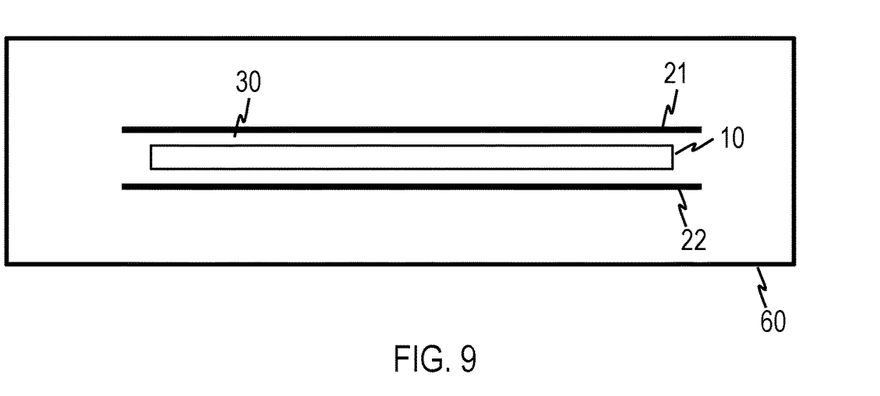
FIG. 9 is a schematic sectional view for explaining the production method according to an embodiment.

As depicted in FIG. 9, the two layers 21, 22 may be connected with each other in an atmosphere with reduced air pressure or in an inert gas atmosphere. The two layers 21, 22, the radiation protection material 10 and possibly present shaped parts 50 or other carrier materials may be placed in a processing chamber 60 in order for the two layers 21, 22 to be connected with each other. The processing chamber 60 may be partially evacuated before the two layers 21, 22 are being connected with each other. Alternatively or additionally, an inert gas atmosphere may be created within the processing chamber 60 before the two layers 21, 22 are being connected with each other.

Figure 10:
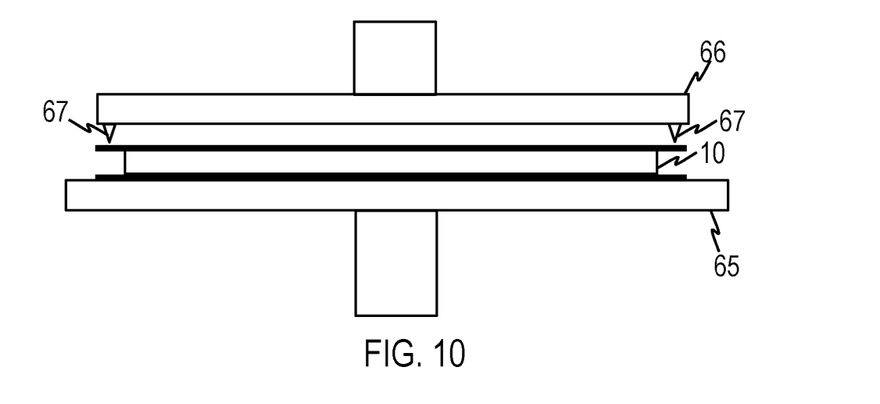
FIG. 10 is a schematic sectional view for explaining the production method according to an embodiment.

As depicted in FIG. 10, an amount of gas in the region between the two layers 21, 22 may be reduced as a machine presses one or both of the layers 21, 22 against the radiation protection material 10 and/or optionally present shaped parts 50 or an optionally present carrier material in a planar manner. This can be carried out in a processing tool for the two layers 21, 22. For instance, a device for welding together the two layers 21, 22 may comprise a stationary or movable contact surface 65 and at least one movable machine component 66 opposing the contact surface 65. Sonotrodes 67 may be provided for high-frequency welding of the layers 21, 22. By moving the machine components 65, 66 toward each other, the layers 21, 22 may be pressed against the radiation protection material 10 or other elements placed between the two layers 21, 22. The amount of gas in the region 30 between the two layers 21, 22 may thus be reduced.

Radiation protection elements 40 according to embodiments may be used in various radiation protection apparatuses in order to provide protection below and above the patient table.

Figure 11:
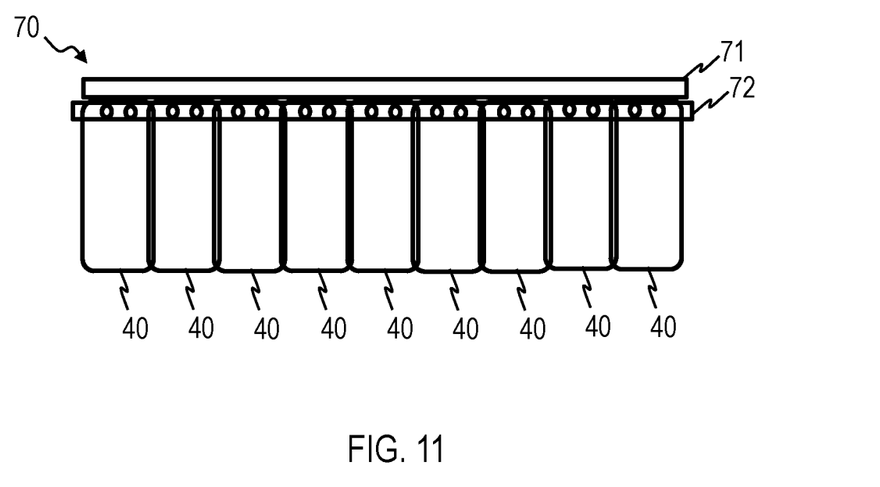
FIG. 11 is a schematic view of a radiation protection apparatus with a radiation protection element according to an embodiment.

FIG. 11 is a schematic view of a patient table 70 with a patient support 71 and a mounting rail 72. A radiation protection element 40 or a plurality of radiation protection elements 40 according to an exemplary embodiment may be mounted on the mounting rail 72. The radiation protection elements 40 may serve as a radiation protection shield for the lower body. Each of the radiation protection elements 40 may be configured as flexible or movably, particularly pivotally arranged panels. The radiation protection shield for the lower body may be formed by one single panel or a plurality of panels arranged in an overlapping manner.

Figure 12:
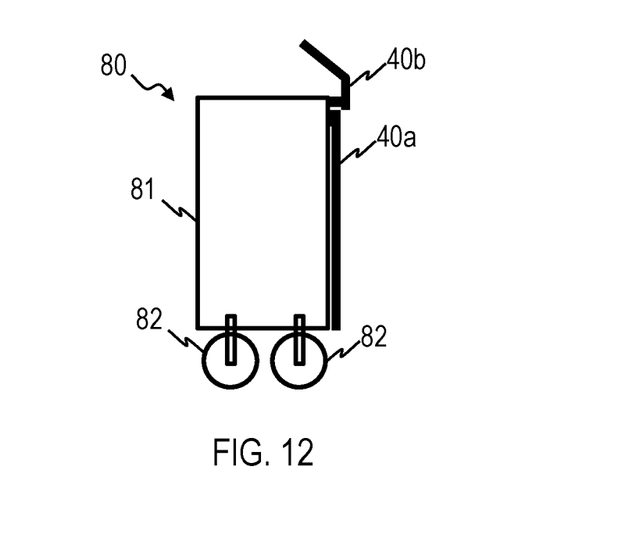
FIG. 12 is a schematic view of a radiation protection apparatus with a radiation protection element according to an embodiment.

FIG. 12 is a schematic view of a radiation protection cart 80. The radiation protection cart 80 comprises a frame 81 and rolls 82 for moving the radiation protection cart 80.

One or a plurality of radiation protection elements 40a according to the invention may be mounted to the radiation protection cart 80 as lower parts of the radiation protection shield. Each of the radiation protection elements 40a may a be flexible or rigid panel. The panels may be mounted rigidly or movably.

Alternatively or additionally, one or a plurality of radiation protection elements 40b according to the invention may be mounted as upper parts to the radiation protection cart 80. The radiation protection elements 40b may comprise a shaped part inside the sheath in order to implement an angled or bent geometry.

Various effects are achieved by the radiation protection elements and methods according to the invention. For instance, the sheath tightly abuts the radiation protection material.

Oxidation processes may be decelerated due to decreased air pockets within the sheath and/or due to inert gas trapped within the sheath. Buckling of the sheath and wrinkling of the sheath may be reduced or completely eliminated.

By way of tight abutment of the sheath on the radiation protection material and optionally present carrier materials, a mechanical support of the radiation protection material may be achieved.

Due to the contact pressure of the sheath against the radiation protection material and shaped parts or other carrier materials present within the sheath, an attachment of the radiation protection material and the carrier material by means of an adhesive may optionally be dispensed with.

Radiation protection elements and corresponding production methods according to the invention may be used for radiation protection elements which are mountable to a patient table or a radiation protection cart. The methods and radiation protection elements according to the invention are not limited to this specific application field but may, e.g., also be used for protective clothing.

Radiation protection elements and corresponding production methods according to the invention may be used for protection against X-ray radiation, particularly with respect to methods of interventional radiology, without being limited thereto.

The invention claimed is:

1. A method for producing a radiation protection element, comprising the steps of:
    arranging at least one radiation protection material between at least two layers of at least one plastic-containing element,
    removing at least part of the gas present between the at least two layers or positioning the at least two layers with the radiation protection material arranged therebetween in an inert gas atmosphere, and
    connecting the at least two layers with each other,
    wherein in a region between the at least two layers a gas pressure is reduced from an initial pressure to a processing gas pressure while the at least two layers are being connected with each other, and
    wherein the processing gas pressure is selected such that inside a sheath of the radiation protection material formed by connecting the at least two layers a gas pressure is less than 1 bar at 23° C.

2. The method according to claim 1, wherein at least one of the layers is pressed toward the radiation protection material in order to remove at least part of the gas present between the at least two layers.

3. The method according to claim 2, wherein at least one of the layers is pressed toward the radiation protection material by means of a movable element of a welding apparatus in order to connect the at least two layers.

4. The method according to claim 1, wherein the at least two layers and the radiation protection material are placed in a processing chamber with a gas pressure reduced relative to an ambient gas pressure or with an inert gas atmosphere.

5. The method according to claim 1, wherein the at least two layers are connected with each other along a connecting line completely or partially extending around the radiation protection material.

6. The method according to claim 5, wherein the at least two layers are connected with each other along an additional connecting line not extending around the radiation protection material.

7. The method according to claim 1, wherein a carrier material and/or a shaped part are additionally incorporated between the at least two layers.

8. The method according to claim 1, wherein the at least one plastic-containing element comprises at least one plastic-containing woven fabric or a polyurethane film.

9. The method according to claim 1, wherein the at least one plastic-containing element or at least one of the two layers is translucent.

10. The method according to claim 1, further comprising the step of attaching a fixing member to the at least two layers for mounting the radiation protection element to a patient table for protection below or above the patient table or to a radiation protection cart.

11. A radiation protection element, comprising:
at least one radiation protection material, and
a sheath with an internal volume in which the at least one radiation protection material is arranged, wherein the internal volume has a negative gas pressure or wherein the internal volume comprises an inert gas,
wherein a gas pressure is less than 1 bar in the internal volume at a temperature of 23° C.

12. The radiation protection element according to claim 11, wherein the sheath comprises a connecting line of two layers of the sheath, said connecting line completely or partially extending around the radiation protection material.

13. The radiation protection element according to claim 12, wherein the sheath comprises an additional connecting line of two layers of the sheath, said additional connecting line not extending around the radiation protection material, wherein the additional connecting line runs around an opening within the sheath.

14. A radiation protection element, comprising:
at least one radiation protection material, and
a sheath with an internal volume in which the at least one radiation protection material is arranged, wherein the sheath planarly abuts the at least one radiation protection material wherein a gas pressure is less than 1 bar in the internal volume at a temperature of 23° C.

15. The radiation protection element according to claim 14, wherein the sheath comprises a connecting line of two layers of the sheath, said connecting line completely or partially extending around the radiation protection material.

16. The radiation protection element according to claim 15, wherein the sheath comprises an additional connecting line of two layers of the sheath, said additional connecting line not extending around the radiation protection material, wherein the additional connecting line runs around an opening within the sheath.

17. A radiation protection apparatus, comprising:
a radiation protection element or a plurality of radiation protection elements, wherein said radiation protection elements comprise at least one radiation protection material, and a sheath with an internal volume in which the at least one radiation protection material is arranged, wherein the internal volume has a negative gas pressure or wherein the internal volume comprises an inert gas.

18. The radiation protection apparatus according to claim 17, wherein the radiation protection apparatus comprises a patient table with a fixing apparatus to which the radiation protection element is mounted for protection below or above the patient table or to which the plurality of radiation protection elements is mounted for protection below or above the patient table, or wherein the radiation protection apparatus comprises a radiation protection cart to which the radiation protection element is mounted or to which the plurality of radiation protection elements is mounted.

19. A radiation protection element, comprising:
at least one radiation protection material, and
a sheath with an internal volume in which the at least one radiation protection material is arranged, wherein the internal volume comprises an inert gas.

* * * * *